(12) United States Patent
Park et al.

(10) Patent No.: US 10,202,596 B2
(45) Date of Patent: Feb. 12, 2019

(54) POROUS MEMBRANE HAVING IMMOBILIZED ENZYME, POROUS MEMBRANE COMPOSITE INCLUDING THE SAME, AND PREPARATION METHOD THEREOF

(71) Applicant: GWANGJU INSTITUTE OF SCIENCE AND TECHNOLOGY, Gwangju (KR)

(72) Inventors: Ji-Woong Park, Gwangju (KR); Sun-Young Han, Gwangju (KR); Jae-Sung Bae, Gwangju (KR)

(73) Assignee: GWANGJU INSTITUTE OF SCIENCE AND TECHNOLOGY, Gwangju (KR)

( * ) Notice: Subject to any disclaimer, the term of this patent is extended or adjusted under 35 U.S.C. 154(b) by 203 days.

(21) Appl. No.: 14/508,414

(22) Filed: Oct. 7, 2014

(65) Prior Publication Data
US 2015/0099288 A1   Apr. 9, 2015

Related U.S. Application Data

(60) Provisional application No. 61/887,482, filed on Oct. 7, 2013.

(30) Foreign Application Priority Data

Jan. 20, 2014  (KR) .................. 10-2014-0006681

(51) Int. Cl.
| | | |
|---|---|---|
| C12N 11/04 | (2006.01) | |
| C12N 11/08 | (2006.01) | |
| C12P 7/64 | (2006.01) | |
| C12P 13/00 | (2006.01) | |
| B01D 71/56 | (2006.01) | |
| B01D 71/64 | (2006.01) | |

(52) U.S. Cl.
CPC .............. *C12N 11/04* (2013.01); *C12N 11/08* (2013.01); *C12P 7/649* (2013.01); *B01D 71/56* (2013.01); *B01D 71/64* (2013.01); *C12P 13/00* (2013.01)

(58) Field of Classification Search
CPC ................................ C12N 11/04; C12N 11/08
See application file for complete search history.

(56) References Cited

U.S. PATENT DOCUMENTS

| | | | |
|---|---|---|---|
| 8,815,967 B2* | 8/2014 | Park ................... | C08G 18/3243 521/162 |
| 9,725,545 B2* | 8/2017 | Wickert ................ | C08F 226/06 |
| 2012/0095123 A1* | 4/2012 | Park ................... | C08G 18/3243 521/163 |

FOREIGN PATENT DOCUMENTS

KR   1020110029748 A   3/2011

OTHER PUBLICATIONS

Moon S-Y; Mo H-R; Ahn M-K; Bae J-S; Jeon E; Park J-W "Organic Sol-Gel Synthesis of Microporous Molecular Networks Containing Spirobifluorene and Tetraphenylmethane Nodes" J. Polym. Sci., Part A: Polym. Chem., 51(8), Apr. 2013 (pub. Online Jan. 28, 2013), pp. 1758-1766, doi: 10.1002/pola.26552. (Year: 2013).*

Han, Sun-Young et al., The Study of Enzymatic Membrane Reactor by Immobilizing Enzyme Into Ultrafiltration Membrane, Conference, Oct. 11-12, 2013, 2 pages, vol. 38, No. 2, Extraordinary General Meeting & Autumn Annual Conference of the Polymer Society of Korea, Changwon Exhibition Convention Center.

* cited by examiner

*Primary Examiner* — Aaron J Kosar
(74) *Attorney, Agent, or Firm* — Hauptman Ham, LLP

(57) ABSTRACT

Disclosed herein is a porous membrane having an immobilized enzyme wherein the enzyme is immobilized within pores which are three-dimensionally connected to each other. The porous membrane having the immobilized enzyme is three-dimensionally crosslinked in a molecular level wherein nanopores of 5 to 100 nm are interconnected, so that the immobilized enzyme may be in contact with a reactant in all directions, and the reaction solution may be easily diffused, thereby proceeding with the catalytic reaction fast and conveniently without deterioration of material transport.

5 Claims, 10 Drawing Sheets

POROUS MEMBRANE HAVING IMMOBILIZED ENZYME, POROUS MEMBRANE COMPOSITE INCLUDING THE SAME, AND PREPARATION METHOD THEREOF

CROSS-REFERENCE TO RELATED APPLICATIONS

This application claims priority to Provisional Application Ser. No. 61/887,482 filed on 7 Oct. 2013, and Korean Patent Application No. 10-2014-0006681 filed on 20 Jan. 2014, and all the benefits accruing there from under 35 U.S.C. § 119, the contents of which is incorporated by reference in its entirety.

TECHNICAL FIELD

The present invention relates to a porous membrane having an immobilized enzyme, and more particularly, to a porous membrane which is an organic porous monolithic organic reticular membrane, three-dimensionally cross-linked in a molecule level, including an immobilized enzyme therein, and a preparation method of the membrane.

BACKGROUND

An enzyme generally has high three-dimensional and chemical selectivity, thereby being useful in various reactions, and is used as a catalyst accelerating a reaction rate even under a mild reaction condition. However, since enzymes are generally costly, they have an economic problem in use in a large amount in an industrial scale. In addition, since most enzymes are insoluble in an organic solvent, they are limited in use in an organic chemical reaction. Therefore, in order to improve activity and stability of the enzyme and reuse the enzyme, research to immobilize the enzyme has much proceeded.

There are largely three ways to immobilize an enzyme on a polymer membrane. The first one is to adsorb an enzyme on a surface of a polymer membrane, the second one is to modify an enzyme to adhere it on a polymer membrane by a covalent bond, and the last one is an entrapping method to physically trap an enzyme in pores of a polymer membrane. Since it is the easiest and simplest way to adsorb an enzyme on a surface of a membrane by a non-covalent bond, much research thereon has been done. However, the enzyme may be easily separated, and the stability of the enzyme is relatively low. Modifying an enzyme and adhering it on a membrane by a covalent bond is the way to most stably immobilize an enzyme. However, since a process of modifying an enzyme is accompanied, the activity of an enzyme is lowered, and a process of immobilizing an enzyme is complicated.

The following patent document 1 relates to a method of immobilizing an enzyme using a double template, wherein the enzyme is immobilized on the double template to show a high catalytic activity. However, the preparation procedure of the catalyst is complicated, and the immobilized enzyme blocks pores, thereby making mass transfer difficult.

RELATED ART DOCUMENT

Patent Document (Patent document 1) Korean Patent Laid-Open Publication No. 2011-0029748

SUMMARY

An object of the present invention is to provide a porous membrane having an immobilized enzyme, which has high immobilization rate and immobilization retention rate of the enzyme, long-term stability of the enzyme activity, and has excellent mass transfer capability.

Another object of the present invention is to provide a preparation method of the porous membrane having an immobilized enzyme, wherein the process of immobilizing the enzyme is simple.

According to an exemplary embodiment of the present invention, there is provided a porous membrane having an immobilized enzyme, wherein the porous membrane is three-dimensionally interconnected by pores, the pores have a size of 5 to 100 nm, and the porous membrane forms a three-dimensional network by polymerization of a monomer having 2 to 4 amino groups and a monomer having 2 to 4 isocyanate groups.

According to an embodiment of the present invention, the porous membrane may be a flat membrane or a hollow fiber membrane.

According to an embodiment of the present invention, the enzyme may be one or more selected from the group consisting of lipase, amylase, protease, trypsin, papain, brinase, peroxidase, horseradish peroxidase (HRP), carbonic anhydrase, aquaporin, chymotrypsin, subtilisin, soybean peroxidase, chloroperoxidase, manganese peroxidase, tyrosinase, laccase, cellulase, xylanase, lactase, sucrase, organophosphohydrolase, chlorinesterase, glucose oxidase, alcohol dehydrogenase, glucose dehydrogenase, hydrogenase, and glucose isomerase.

According to another exemplary embodiment of the present invention, there is provided a preparation method of the porous membrane having an immobilized enzyme, wherein the porous membrane is penetrated with a solution containing the enzyme.

DETAILED DESCRIPTION OF EMBODIMENTS

Figure 1:
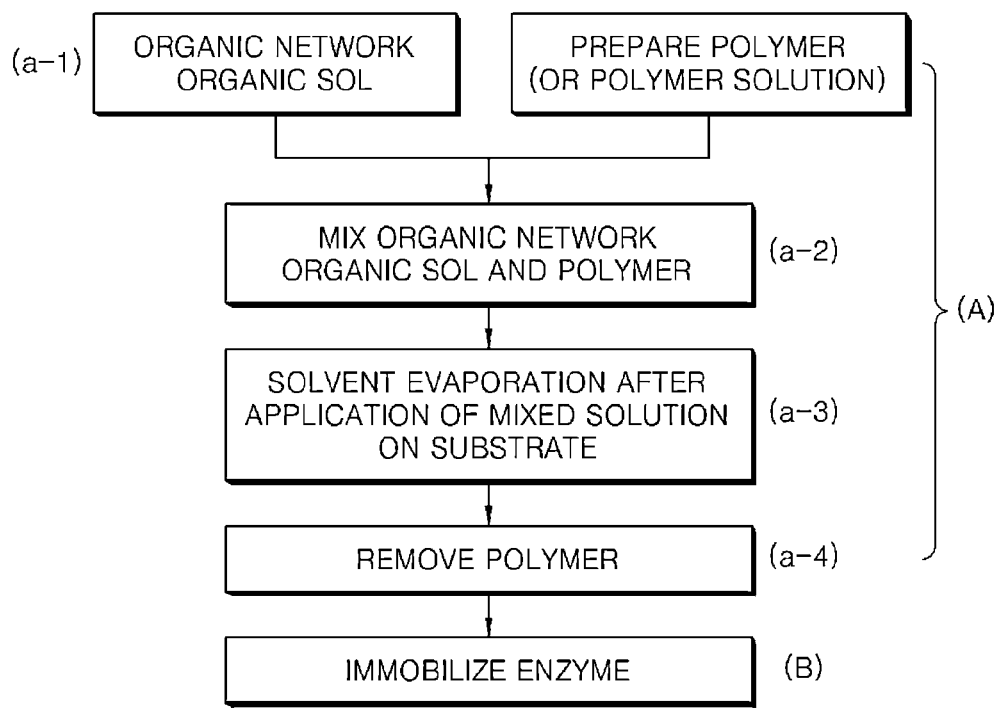
FIG. 1 is a flow chart representing a process of preparing the porous membrane having the immobilized enzyme of the present invention.

Hereinafter, the present invention will be described in detail. Herein, it should be understood that the terms such as "first" and "second" are used not for limiting, but for distinguishing the constituents of the invention.

The porous membrane having an immobilized enzyme according to the present invention includes a porous membrane forming a three-dimensional reticular nanopores, and an enzyme captured within pores of the porous membrane.

The porous membrane forms a three-dimensionally cross-linked monolith, and includes pores having a size of 5 to 100 nm, wherein the pores are interconnected, so that the enzyme immobilized therein may be in contact with a reactant in all directions, and the solution may be easily diffused, and thus, reduction in material transport, caused by the enzyme blocking pores, does not occur.

Further, the size of pores of a porous carrier for immobilizing an enzyme therein is generally known to be 20 to 50 nm (Membrane-Based Synthesis of Nanomaterials, Charles R. Martin), and since the porous membrane of the present invention has wide range of nanopores of 5 to 100 nm, it may immobilize the enzyme having various sizes.

The enzyme which may be immobilized in the porous membrane of the present invention may be specifically a digestive enzyme such as lipase, amylase or protease, a proteolytic enzyme such as trypsin, papain or brinase, or the like, and peroxidase, horseradish peroxidase (HRP), or the like may be used for water treatment. Further, carbonic anhydrase may be used for capturing carbon dioxide. Additionally, the enzyme may be one or more selected from the group consisting of aquaporin, chymotrypsin, subtilisin, soybean peroxidase, chloroperoxidase, manganese peroxidase, tyrosinase, laccase, cellulase, xylanase, lactase, sucrase, organophosphohydrolase, chlorinesterase, glucose oxidase, alcohol dehydrogenase, glucose dehydrogenase, hydrogenase, and glucose isomerase, but not limited thereto.

The porous membrane of the present invention may be obtained by mixing an organic sol consisting of an organic reticular structure obtained by polymerizing a first monomer having an amino group and a second monomer having an isocyanate group, an acyl halide group or an ester group which is a functional group polymerizable with the amino group, with a polymer to produce a porous membrane via phase separation into the polymer and organic sol phases and the subsequent gelation of organic sol phase, and removing the polymer from the porous membrane using a solvent that dissolves the polymer.

According to an embodiment of the present invention, the first monomer has 2 to 4 amino groups, and the second monomer has functional groups selected from the group consisting of 2 to 4 isocyanate groups, acyl halide groups and ester groups.

The first monomer having 2 to 4 amino groups may be an aliphatic compound having 1 to 100 carbons, substituted with 2 to 4 amino groups, or an aromatic compound having 6 to 100 carbons, substituted with 2 to 4 amino groups.

The second monomer having 2 to 4 isocyanate groups, acyl halide groups or ester groups may be an aliphatic compound having 1 to 100 carbons, substituted with 2 to 4 isocyanate groups, acyl halide groups or ester groups, or an aromatic compound having 6 to 100 carbons, substituted with 2 to 4 isocyanate groups, acyl halide groups or ester groups.

The first and second monomers may be, as an example, compounds represented by the following Chemical Formulae 1 to 9:

[Chemical Formula 1]

[Chemical Formula 2]

[Chemical Formula 3]
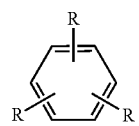

[Chemical Formula 4]
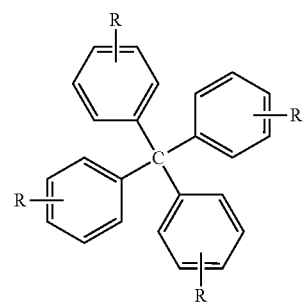

[Chemical Formula 5]
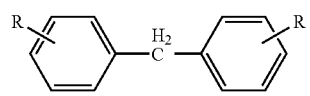

[Chemical Formula 6]
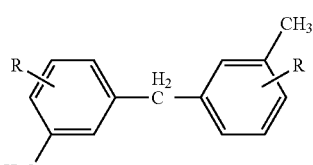

[Chemical Formula 7]
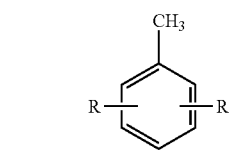

[Chemical Formula 8]
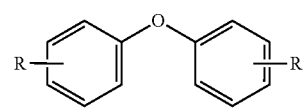

[Chemical Formula 9]

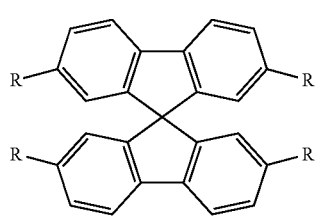

wherein R is an amino group, an isocyanate group, an acyl halide group, or an ester group.

Further, according to an embodiment of the present invention, the first and second monomers may be the compound represented by the following Chemical Formula 10:

[Chemical Formula 10]

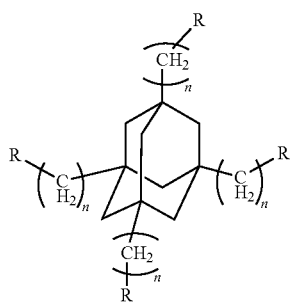

wherein R is an amino group, an isocyanate group, an acyl halide group, or an ester group; and n is 0 or 1.

The first monomer and the second monomer are polymerized by reaction between the amino group of the first monomer and the isocyanate group, the acyl halide group or the ester group of the second monomer, to generate a crosslinked network.

That is, the organic reticular structure formed by the polymerization between the first monomer and the second monomer is three-dimensionally polymerized and cross-linked to have micropores and a large specific surface area, and has excellent chemical resistance, thermal resistance and durability by a high crosslinking rate and a strong covalent bond.

Further, the monomer having 2 to 4 amino groups may be, as an example, tetratis(4-aminophenyl)methane (TAPM), p-phenylene diamine (PDA), or oxydianiline (4,4'-oxydianiline) (ODA), but not limited thereto.

Further, the monomer having 2 to 4 isocyanate groups may be, as an example, p-phenylene diisocyanate (PDI), hexamethylene diisocyanate (HDI), or tetrakis(4-isocyanatophenyl)methane (TIPM), but not limited thereto.

According to an embodiment of the present invention, the porous membrane may be formed by polymerization of the monomer represented by the following Chemical Formula 11 and the monomer having 2 isocyanate groups:

[Chemical Formula 11]

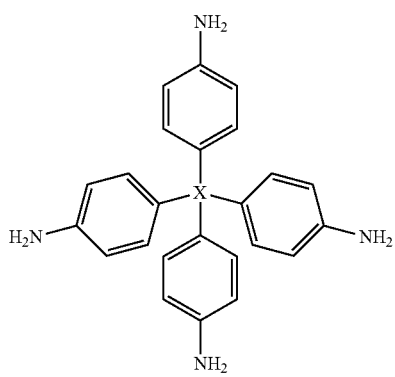

wherein X is a carbon or silicon atom.

Further, according to another embodiment of the present invention, the porous membrane may be formed by polymerization of the monomer having 2 amino groups and the monomer represented by the following Chemical Formula 12:

[Chemical Formula 12]

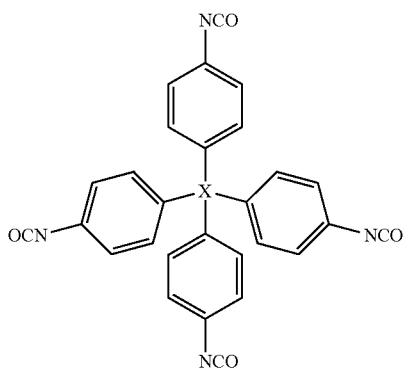

wherein X is a carbon or silicon atom.

The porous membrane may have a structure of a flat membrane or a hollow fiber membrane.

Further, the present invention provides a preparation method of a porous membrane having an immobilized enzyme, including (B) passing a solution containing the enzyme through the porous membrane, wherein the enzyme is immobilized within the pores of the porous membrane.

When the porous membrane is penetrated with the solution containing the enzyme, the solution passes through the porous membrane, and in the course of which the enzyme flowing along with the solution is captured in the pores having a similar size within the membrane, by gravity or optionally applied pressure. The thus-captured enzyme is physically immobilized by a noncovalent bond with the porous membrane.

The passing of the solution may be carried out in a manner selected from dead-end flow, cross flow filtration, or the combination thereof, and the immobilization rate of the enzyme may be further increased by applying pressure.

According to an embodiment of the present invention, the immobilization level of the enzyme may be much raised by additionally passing a solvent for enzyme immobilization through the porous membrane having the immobilized enzyme. The solvent for enzyme immobilization may be water.

However, such additional step does not necessarily have to be carried out separately, and for example, in case where an enzyme for preparing biodiesel is immobilized, biodiesel may be prepared without an outflow of the enzyme, by including a raw material of biodiesel in the solvent for enzyme immobilization and passing it. Such preparation method of the porous membrane may include (A) obtaining the porous membrane, before (B).

Said (A) may include the following: (a-1) polymerizing the monomer having 2 to 4 amino groups and the monomer having 2 to 4 isocyanate groups, acyl halide groups or ester groups to obtain an organic sol, (a-2) adding a polymer solution to the organic sol to obtain a mixed solution, (a-3) applying the mixed solution onto a substrate then curing it to obtain a network/polymer composite membrane, and (a-4) passing solvent through the microporous membrane or immersion of the membrane into solvent to remove polymers, thereby forming a porous membrane including nanopores.

The polymer solution is prepared by dissolving a thermoplastic polymer in a suitable solvent such as DMF, DMAc, NMP, DMSO, THF and ethanol, and the polymer may be any one selected from the group consisting of polyethyleneglycol, polysulfone, polyethersulfone, polyacrylonitrile, polyimide, polyetherimide, polybenzimidazole, polymethylmethacrylate, polystyrene, polyetheretherketone and polyvinylidenefluoride.

The pore size and the microstructure of the porous membrane are adjustable according to the amount of the polymer solution added to the organic sol in above (a-2). As the amount of the polymer solution is increased, the phase separation between the organic network sol and the polymer solution much proceeds, thereby making the pores larger.

The solution containing the organic reticular structure formed by polymerization of the first monomer having 2 to 4 amino groups and the second monomer having 2 to 4 isocyanate groups, acyl halide groups or ester groups, may proceed with gelation, as it has higher degrees of polymerization and crosslinking. However, since a gelation rate depends on the concentration of the mixed monomers, the solution is controllable to the organic sol state which is an intermediate state before gelation, by properly adjusting the concentration of the monomer solution.

Therefore, in the preparation of the porous membrane (A), the resulting porous membrane may have various structures and sizes, by a gelation reaction and a phase separation phenomenon between the organic sol and the polymer solution. The structure of the porous membrane is controllable in the course of preparing the organic sol by the factors such as polymerization time of the monomers, the property of the prepared organic reticular structure (a covalent bonding or physical bonding property within the organic network), the kind and the molecular weight of the polymer added to the sol, and the compositional ratio between the organic network and the polymer. Therefore, by properly adjusting such factors, the porous membrane having a desired property depending on its use may be selectively prepared.

In above (a-3), the solvent may be removed from the mixed solution before the mixed solution is applied on the substrate. On removing the solvent from the mixed solution, the gelation may slowly proceed, thereby making the size of the pores larger.

Further, in above (a-3), the mixed solution may be applied by properly selecting one of the solution processes such as spin coating, dip coating, spray coating, casting and doctor blade coating, considering the viscosity of the mixed solution and the like.

Further, the present invention provides a preparation method of biodiesel, including carrying out a reaction in a reaction solution containing (a) a biodiesel raw material, (b) the porous membrane, and (c) a solvent.

The biodiesel raw material may be a mixture of soybean oil and ethanol, the enzyme immobilized within the porous membrane may be lipase, and the solvent may be an organic solvent.

Hereinafter, the present invention is illustrated by the following preferred Examples, and the like, in more detail. However, those Examples and the like are intended to describe the present invention in more detail, and it will be evident to a person skilled in the art that the scope of the present invention is in no way limited thereby.

EXAMPLES

Example 1: Preparation of Porous Membrane (1) Preparation of (TAPM+HDI/PEG) Nanocomposite Membrane Tetrakis(4-aminophenyl) methane (TAPM, MW:382.50) was dissolved in DMF (N,N-dimethylformaide) to prepare an organic solution having a concentration of 4 wt/vol %, and 1,6-diisocyanatohexane (HDI; hexamethylene diisocyanate, MW:168.19) was dissolved in DMF to prepare an organic solution having a concentration of 4 wt/vol %. Then, the tetra(4-aminophenyl) methane solution was slowly injected to the 1,6-diisocyanatohexane solution and mixed. The above mixed solution was reacted at room temperature under nitrogen atmosphere for 72 hours to obtain a sol-phase mixed solution.

After adding polyethylene glycol (PEG) to the mixed solution in a concentration of 60 wt % and sufficiently stirring it, the mixture was applied on a glass plate, and dried and cured at 50° C. for 1 hour, at 80° C. for 2 hours, and at 100° C. for 3 hours, thereby finally synthesizing the nanocomposite membrane of the organic molecular network (TAPM+HDI) and PEG.

(2) Preparation of TAPM+HDI Porous Membrane—Removal of PEG

Figure 8:
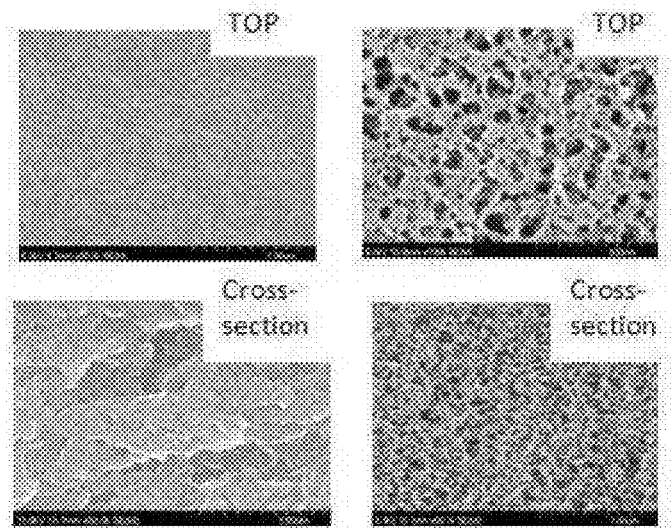
FIG. 8 is a SEM (scanning electron microscopic) image representing the porous membrane prepared according to an exemplary embodiment of the present invention before and after removal of polyethylene glycol (PG) from the membrane.

After the synthesized membrane was cooled down at room temperature, it was precipitated in water to be separated from the substrate, and stirred in water for about one week to remove polyethylene glycol (PEG) which is water-soluble polymer. Thus, finally the porous membrane having nanopores according to the present invention was prepared. The SEM images of the membrane before and after removing polyethylene glycol are shown in FIG. 8. As shown in FIG. 8, it was confirmed that the porous membrane was formed by leaving voids in the place where PEG had been located, after removal of PEG.

(3) Immobilization of Enzyme

The porous membrane having an immobilized enzyme of the present invention was prepared using lipase as the enzyme.

After preparing a solution formed by dispersing lipase in water (90 mg/L), undissolved lipase was removed using a cellulose acetate membrane filter of 0.22 μm, then the porous membrane prepared in above (2) was penetrated with the thus prepared solution in a manner of dead-end flow, thereby preparing the porous membrane having immobilized lipase.

Figure 2:
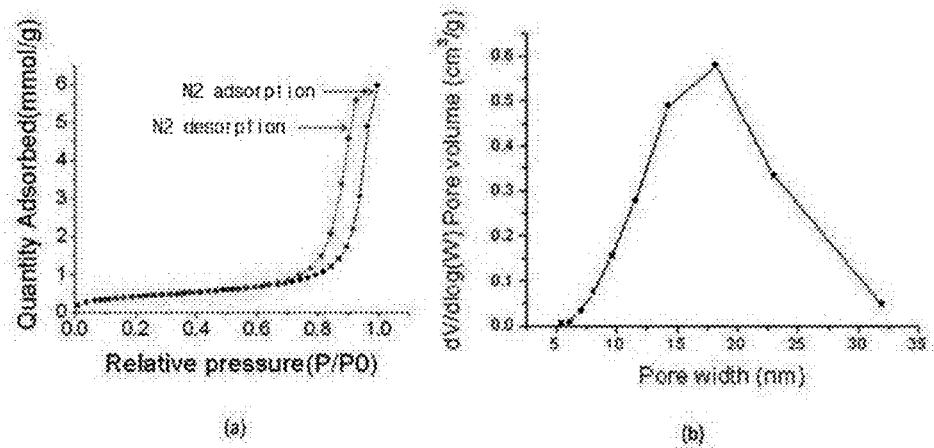
FIG. 2(a) is a graph representing nitrogen adsorption/desorption curves of the porous membrane having immobilized lipase according to an exemplary embodiment of the present invention.
FIG. 2(b) is a graph representing a pore size distribution of the porous membrane having immobilized lipase according to an exemplary embodiment of the present invention.
Figure 3:
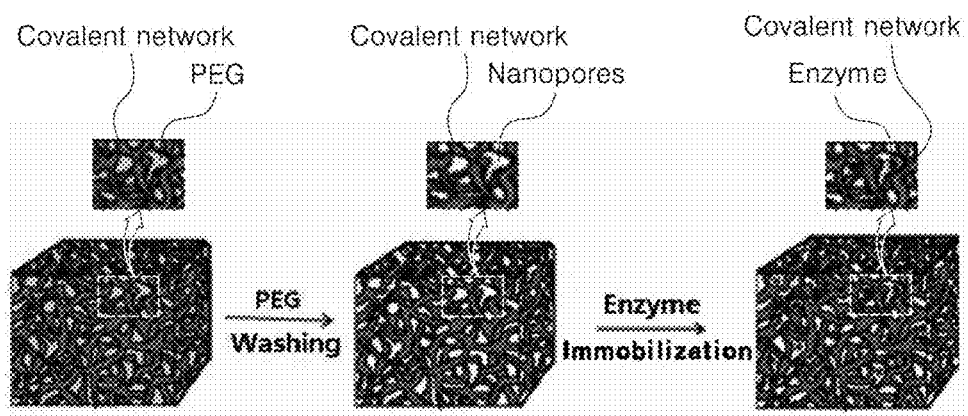
FIG. 3 is a schematic diagram of the preparation method of the membrane having the immobilized enzyme of the present invention.

Confirmation Example 1: Measurement of Pore Size of Membrane Having Immobilized Lipase The presence, size and distribution of the pores formed by removing PEG from the composite membrane consisting of TAPM/HDI and PEG were confirmed through a specific surface area analyzer. FIG. 2(a) is a graph representing nitrogen adsorption/desorption curves, and FIG. 2(b) is a graph representing a pore size distribution. As shown in FIG. 2(b), it was confirmed that the pores formed by removing PEG which is a polymer matrix had various sizes of 5 to 100 nm, and an average size of 20 nm.

Confirmation Example 2: FT-IR Measurement

Figure 4:
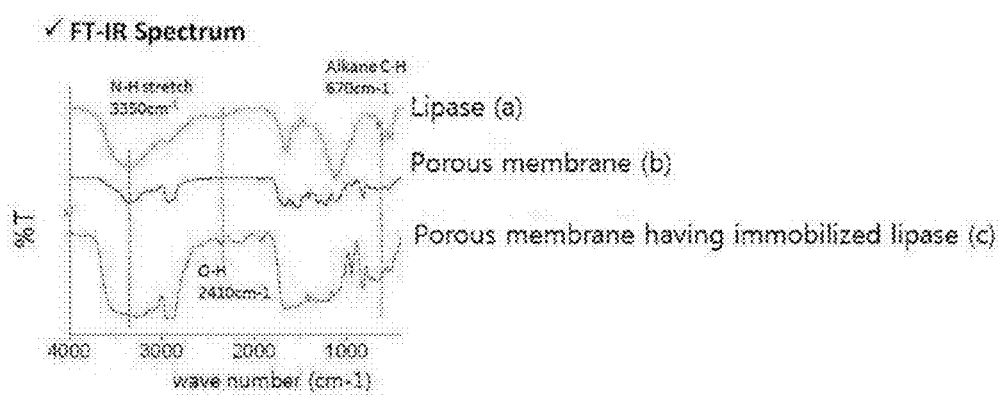
FIG. 4 is a FT-IR spectrum of the porous membrane prepared according to an exemplary embodiment of the present invention.

FIG. 4 is a FT-IR spectroscopy (Fourier Transform Infrared Spectroscopy) spectrum of lipase, the porous membrane before immobilizing the enzyme (lipase), and the porous membrane having the immobilized enzyme (lipase) prepared according to an exemplary embodiment of the present invention. The membrane prepared according to the present invention (c) has a broader peak at 3350 $cm^{-1}$ than the membrane before immobilizing lipase (b), which is resulted from an amino group (—NH) of amino acid in lipase which is the immobilized enzyme. Further, the peak at 2410 $cm^{-1}$ was caused by a carboxyl group (—COOH) of lipase, and the increased peak at 670 $cm^{-1}$ was caused by a CH group in an alkyl chain of lipase. Thus, it is confirmed that the porous membrane of the present invention has immobilized lipase which is the enzyme.

Confirmation Example 3: Confocal Microscopic Image Measurement

Figure 5:
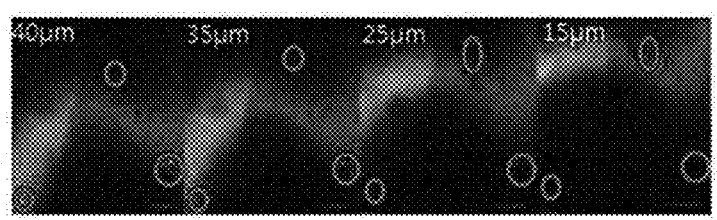
FIG. 5 is a confocal microscopic image of the porous membrane prepared according to an exemplary embodiment of the present invention.

In order to confirm whether the enzyme was dispersed and immobilized inside the porous membrane prepared in one exemplary embodiment of the present invention, the membrane was applied with green fluorescent protein, and examined by a confocal microscope. Each image in FIG. 5 is a photograph taken by focusing at a point 40, 35, 25, 15 and 5 μm away from the membrane surface of the present invention, respectively. As the focusing point changes, the fluorescent protein which at first had been observed became invisible, and the fluorescent protein which at first had not been observed became visible. This means that the fluorescent proteins were distributed evenly throughout the porous membrane, respectively.

Experimental Example 1: Measurement of Amount of Immobilized Enzyme

Figure 6:
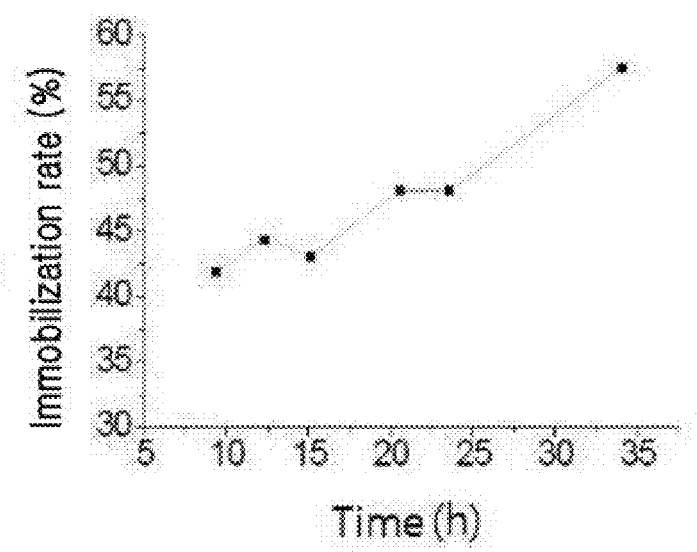
FIG. 6 is a graph representing an amount of an enzyme immobilized on the porous membrane over time.

The amount of the enzyme immobilized in the membrane prepared according to an exemplary embodiment of the present invention was measured using a BCA kit. FIG. 6 is a graph representing an amount of an enzyme immobilized in the porous membrane over time. As shown in FIG. 6, as penetration time increased, the amount of the immobilized enzyme also increased. As a result of measuring the absorbance with the solution taken after penetration of the enzyme solution for 10 hours, the concentration of the enzyme solution was reduced by about 40% as compared with the initial solution, and in case of the solution taken for 35 hours, the concentration was reduced by about 60% as compared with the initial solution. This means that more than about 40% of the enzyme of the solution was immobilized in the porous membrane after penetration time of 10 hours, and about 60% of the enzyme of the solution was immobilized in the porous membrane after penetration time of 35 hours.

Experimental Example 2: Measurement of Enzyme Activity and Stability

In order to measure the catalytic activity of the enzyme immobilized in the porous membrane prepared according to an exemplary embodiment of the present invention, oleic acid and butanol were used as reactants. The oleic acid and butanol are converted to butyloleate by esterification. The conversion rate of the oleic acid was calculated by titrating the mixture of oleic acid and butanol which is the starting material, and the solution penetrating the porous membrane of the present invention with a potassium hydroxide solution, and the activity of the enzyme was measured using the conversion rate.

Figure 9:
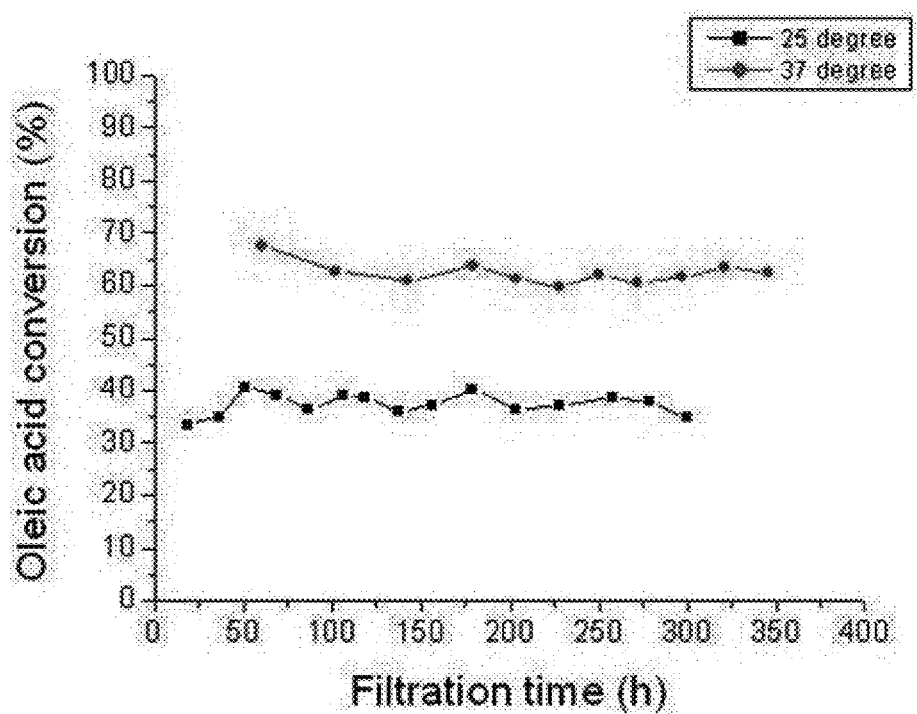
FIG. 9 is a graph representing an oleic acid conversion rate over penetration time of the porous membrane prepared according to an exemplary embodiment of the present invention.

Further, it was confirmed that the oleic acid conversion rate was well maintained on continuous operation of the membrane for a long time by passing the mixture of oleic acid and butanol through the porous membrane having the immobilized enzyme of the present invention. FIG. 9 is a graph representing the oleic acid conversion rate according to the penetration time of the mixture through the porous membrane having the immobilized enzyme prepared according to an exemplary embodiment of the present invention at 25 and 37° C. It was confirmed that at 25° C., the oleic acid conversion rate was maintained at about 37% even for the mixture penetration time of 300 hours or more, and at 37° C. which is known to be an optimal activity temperature of the lipase enzyme, the oleic acid conversion rate was significantly increased to maintain at about 63%. Hereby, the stability of the immobilized enzyme may be verified.

Figure 10:
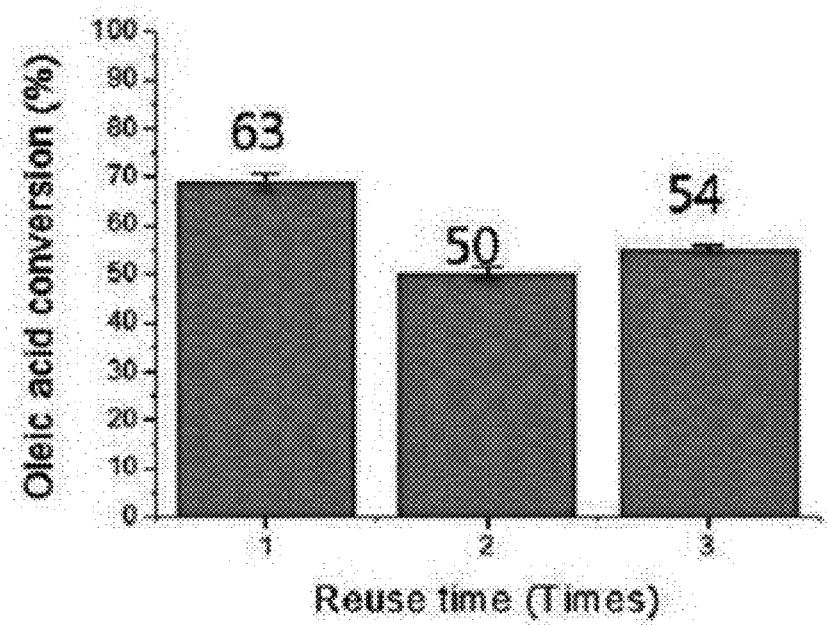
FIG. 10 is a graph representing an oleic acid conversion rate according to the number of reuse of the porous membrane prepared according to an exemplary embodiment of the present invention.

Further, the porous membrane of the present invention is reusable, and FIG. 10 is a graph representing an oleic acid conversion according to the number of reuse of the porous membrane prepared according to an exemplary embodiment of the present invention. The conversion rate was 63% when the membrane was used once 50% when used twice, and 54% when used three times. Each time the membrane was used continuously by flowing reactants for 300 hours and then stored in a refrigerator before next use. As the number of use is increased, the conversion rate was slightly lowered as compared with the conversion rate of first use, but still high as compared with the case without the porous membrane.

Example 2: Preparation of Biodiesel

Figure 7:
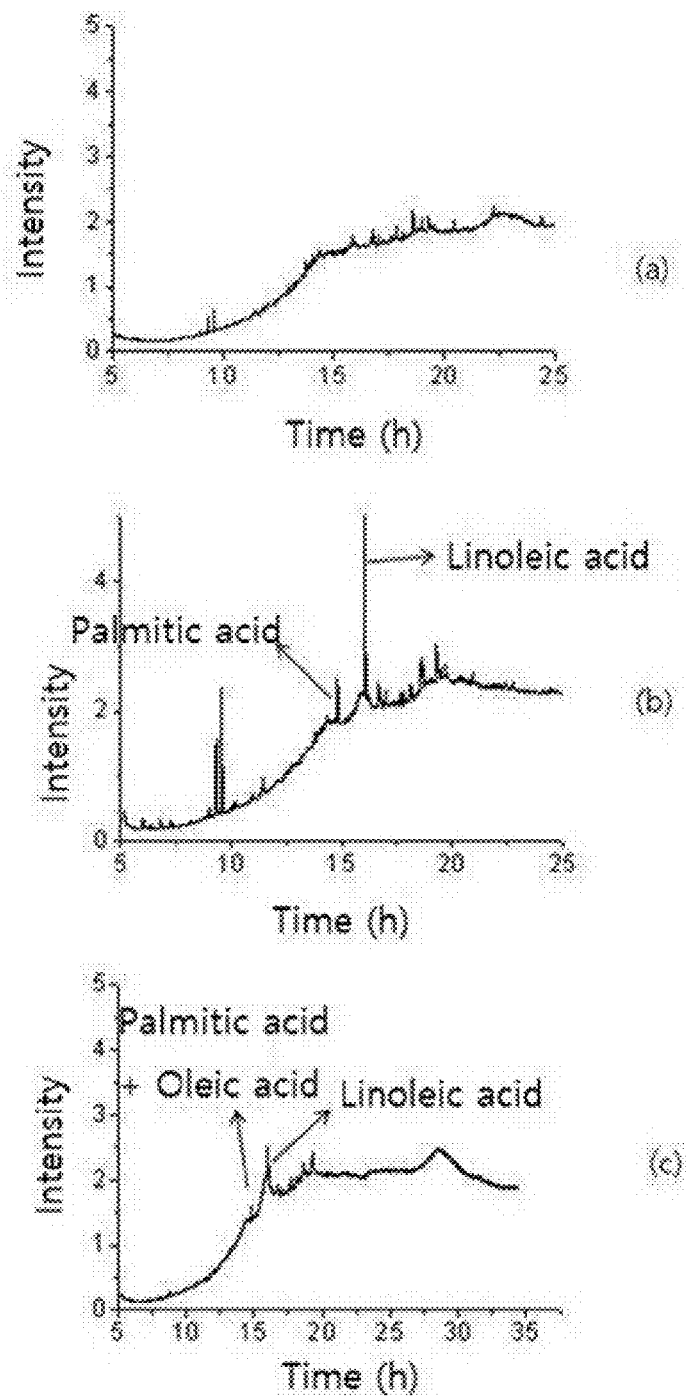
FIGS. 7(a) to 7(c) is a graph representing the result of measuring each solution by a gas chromatography in Example 2.

Biodiesel was prepared using the porous membrane prepared according to Example 1. (a) A mixed solution of 1 mol of soybean oil and 4 mol of ethanol, (b) a solution formed by directly adding lipase to the mixed solution of 1 mol of soybean oil and 4 mol of ethanol to cause reaction, and (c) a solution obtained by passing the mixed solution of 1 mol of soybean oil and 4 mol of ethanol through the porous membrane having immobilized lipase, were measured by a gas chromatography, and the result is shown in FIG. 7. As shown in FIG. 7, it was confirmed that materials in the form of fatty acid ethyl ester which is usable as biodiesel were produced in the cases of the solution passed through porous membrane having immobilized lipase of the present invention ((b) in FIG. 8) and the solution to which lipase was added ((c) in FIG. 8), but not in the case of the absence of lipase ((a) in FIG. 8). This means that lipase acted as a transesterification reaction catalyst.

Further, the spectrum peak intensity of solution (b) penetrating the porous membrane of the present invention was higher than that of solution (c) to which lipase was added. This means that the catalytic activity of the porous membrane having immobilized lipase of the present invention is higher, and such result was generated from the fact that if the reactants are mixed directly with lipase, lipase is not mixed well with the reactant, so that the reaction is generated only in a limited boundary surface, whereas if lipase is immobilized within the porous membrane through which the reactant is passed, the contact area of the reactant and lipase is increased, thereby more activating the catalyst reaction.

The porous membrane having an immobilized enzyme of the present invention has a high immobilization rate of the enzyme, caused by having a large surface area, and low resistance to mass transfer, caused by the fact that due to a three-dimensional pore structure through which reactants are movable, and thus, the immobilized enzyme has excellent catalytic activity.

The porous membrane having an immobilized enzyme of the present invention are highly stable against both organic or aqueous solvent because the pore structure are built upon a three-dimensional covalent network and thus the pore dimension and shape is not swollen or collapsed by the chemicals.

What is claimed is:

1. A porous membrane having an immobilized enzyme, wherein
the porous membrane is three-dimensionally interconnected by pores, the pores have a size of 5 nm to 100 nm,
a framework of the porous membrane is a three-dimensional network formed by polymerization of a first monomer and a second monomer, wherein the first monomer is tetrakis(4-aminophenyl) methane (TAPM), and the second monomer is hexamethylene diisocyanate (HDI), and
the three-dimensional network is formed by polymerization occurring by reacting the first monomer with the second monomer.

2. The porous membrane of claim 1, wherein the porous membrane has a thickness of 10 μm to 100 μm.

3. The porous membrane of claim 1, wherein the porous membrane has a structure of a flat membrane or a hollow fiber membrane.

4. The porous membrane of claim 1, wherein the enzyme is one or more selected from the group consisting of lipase, amylase, protease, trypsin, papain, brinase, peroxidase, horseradish peroxidase (HRP), carbonic anhydrase, aquaporin, chymotrypsin, subtilisin, soybean peroxidase, chloroperoxidase, manganese peroxidase, tyrosinase, laccase, cellulase, xylanase, lactase, sucrase, organophosphohydrolase, chlorinesterase, glucose oxidase, alcohol dehydrogenase, glucose dehydrogenase, hydrogenase, and glucose isomerase.

5. A multiple layered membrane having a structure wherein two or more of the porous membranes of claim 1 are overlaid.

* * * * *